United States Patent
Liang et al.

(10) Patent No.: US 10,431,001 B2
(45) Date of Patent: Oct. 1, 2019

(54) METHOD AND SYSTEM FOR INTERACTIVE PERCUTANEOUS PRE-OPERATION SURGICAL PLANNING

(75) Inventors: Cheng-Chung Liang, West Windsor, NJ (US); Guo-Qing Wei, Plainsboro, NJ (US); Li Fan, Belle Mead, NJ (US); Jianzhong Qian, Princeton Junction, NJ (US); Hong Chen, Plainsboro, NJ (US); Feng Ma, Pennington, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 919 days.

(21) Appl. No.: 12/275,699

(22) Filed: Nov. 21, 2008

(65) Prior Publication Data

US 2009/0142740 A1    Jun. 4, 2009

Related U.S. Application Data

(60) Provisional application No. 60/989,580, filed on Nov. 21, 2007.

(51) Int. Cl.
*G06T 19/00* (2011.01)
*A61B 34/10* (2016.01)
*G16H 50/50* (2018.01)

(52) U.S. Cl.
CPC .............. *G06T 19/00* (2013.01); *A61B 34/10* (2016.02); *A61B 2034/102* (2016.02);
(Continued)

(58) Field of Classification Search
CPC ...... G09B 23/285; G09B 23/28; G09B 23/30;
A61B 19/50; A61B 19/5244; A61B 2019/507; A61B 19/56; A61B 2019/505; A61B 2019/5291; A61B 34/10; A61B 2034/102; A61B 2034/105; G06F 19/3437; G06F 19/3406; G06F 19/3481; G06T 19/00; G06T 2210/41; G06T 2210/21; G16H 50/50
(Continued)

(56) References Cited

U.S. PATENT DOCUMENTS 6,064,904 A * 5/2000 Yanof et al. .................. 600/414
6,426,745 B1 * 7/2002 Isaacs ................. G06F 3/04845
345/419

(Continued)

FOREIGN PATENT DOCUMENTS

WO    WO 2007/053676 A2    5/2007

OTHER PUBLICATIONS

InnovMETRIC Software Inc., "PolyWorks® V10 Beginner's Guide", Feb. 2007, InnovMETRIC Software Inc., pp. 1-121.*
(Continued)

*Primary Examiner* — Jack Yip
(74) *Attorney, Agent, or Firm* — Pillsbury Winthrop Shaw Pittman

(57) ABSTRACT

The success of percutaneous radiofrequency ablation mainly depends on the accuracy of the needle insertion, making it possible to destroy the whole tumor, while avoiding damages on other organs and minimizing risks of a local recurrence. This invention presents a simulated 3D environment for user to interactively place a treatment probe to a target position.

24 Claims, 17 Drawing Sheets

(52) U.S. Cl.
CPC ..... *A61B 2034/105* (2016.02); *G06T 2210/21* (2013.01); *G06T 2210/41* (2013.01); *G16H 50/50* (2018.01)

(58) Field of Classification Search
USPC ....... 434/219, 262, 267, 272, 323, 365, 403, 434/429
See application file for complete search history.

(56) References Cited

U.S. PATENT DOCUMENTS

| | | | |
|---|---|---|---|
| 7,236,618 B1* | 6/2007 | Chui et al. | 382/128 |
| 7,315,304 B2 | 1/2008 | Liang et al. | |
| 2001/0031920 A1* | 10/2001 | Kaufman | A61B 5/055 |
| | | | 600/431 |
| 2003/0032878 A1* | 2/2003 | Shahidi | 600/429 |
| 2004/0009459 A1* | 1/2004 | Anderson et al. | 434/262 |
| 2004/0233223 A1* | 11/2004 | Schkolne | G06F 3/0346 |
| | | | 345/621 |
| 2005/0015005 A1* | 1/2005 | Kockro | 600/427 |
| 2005/0043609 A1* | 2/2005 | Murphy et al. | 600/408 |
| 2005/0174347 A1 | 8/2005 | Visser | |
| 2006/0020206 A1* | 1/2006 | Serra | A61B 8/00 |
| | | | 600/447 |
| 2006/0142657 A1* | 6/2006 | Quaid | A61B 17/1764 |
| | | | 600/424 |
| 2007/0103464 A1* | 5/2007 | Kaufman | G06T 7/0012 |
| | | | 345/424 |
| 2007/0239150 A1 | 10/2007 | Zvuloni et al. | |
| 2007/0248261 A1 | 10/2007 | Zhou et al. | |
| 2009/0036902 A1* | 2/2009 | DiMaio | A61B 8/12 |
| | | | 606/130 |
| 2009/0253109 A1* | 10/2009 | Anvari et al. | 434/262 |
| 2009/0318804 A1* | 12/2009 | Avital et al. | 600/439 |
| 2010/0261526 A1* | 10/2010 | Anderson | G06F 3/016 |
| | | | 463/31 |

OTHER PUBLICATIONS

Acuity Lighting Group, "Visual Release 2.4 Professional Edition User's Guide", Aug. 15, 2006, http://www.visual-3d.com/support/documentation.aspx, pp. 1-181.*

International Search Report and Written Opinion of the International Searching Authority issued in International Patent Application No. PCT/US2008/084324 dated Nov. 21, 2008.

European Search Report corresponding to European Serial No. 08852922.7 dated Nov. 23, 2012.

Office Action dated Apr. 19, 2018 in U.S. Appl. No. 14/926,559.

* cited by examiner

METHOD AND SYSTEM FOR INTERACTIVE PERCUTANEOUS PRE-OPERATION SURGICAL PLANNING

RELATED APPLICATION

The present invention claims priority of provisional patent application No. 60/989,580 filed Nov. 21, 2007, the contents of which are incorporated herein in their entirety.

BACKGROUND OF THE INVENTION

2. Field of the Invention

The present teaching relates to method and system for medical image processing and methods and systems incorporating the present teaching. More specifically, the present teaching relates to method and system for interactive medical image processing and methods and systems incorporating the present teaching.

3. Description of Related Art

With the advancements made in the field of medical imaging, minimally invasive techniques for the ablation of liver tumors have been made possible. Among such minimal invasive techniques, percutaneous thermal ablation has been studied in different forms. Currently, percutaneous radiofrequency ablation is one of the most promising alternatives to open surgery for the treatment of liver cancer. This operation is a minimally invasive procedure in which a needle is inserted into targeted tissues that are destroyed by heat. This modality has been introduced for treating patients who have non-resectable hepatic metastases. The success of such an operation depends largely on the accuracy of the needle insertion because when it is accurate, it is possible to destroy the whole tumor without damaging nearby organs so as to minimize the risks of a local recurrence. To ensure accuracy, a preoperative treatment planning is usually performed, which is one of the crucial factors in avoiding complications or even deaths.

Conventionally, a radiologist who performs a preoperative treatment planning relies on images of 2D scanned slices to determine the positioning of the needles. Unfortunately, this makes the planning of such a treatment rather difficult when relying only on 2D scanner slices. Therefore, there is a need for a solution which can be used to assist a medical personnel to perform a preoperative treatment planning in a more reliable and accurate manner.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION OF THE PRESENT TEACHING

Figure 1A:
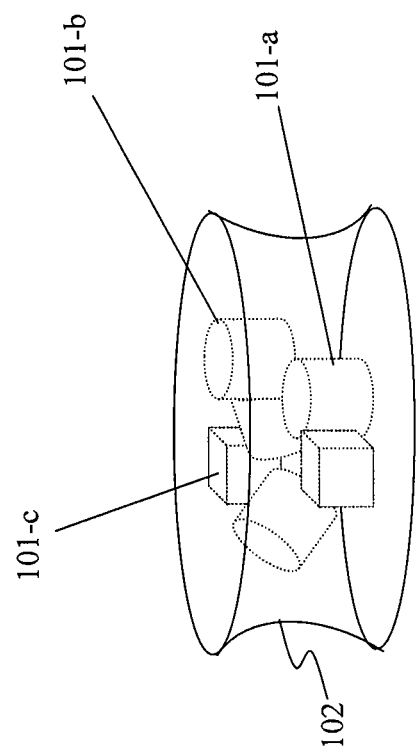
FIG. 1(a) depicts a three dimensional (3D) volume having 3D objects contained therein.
Figure 1B:
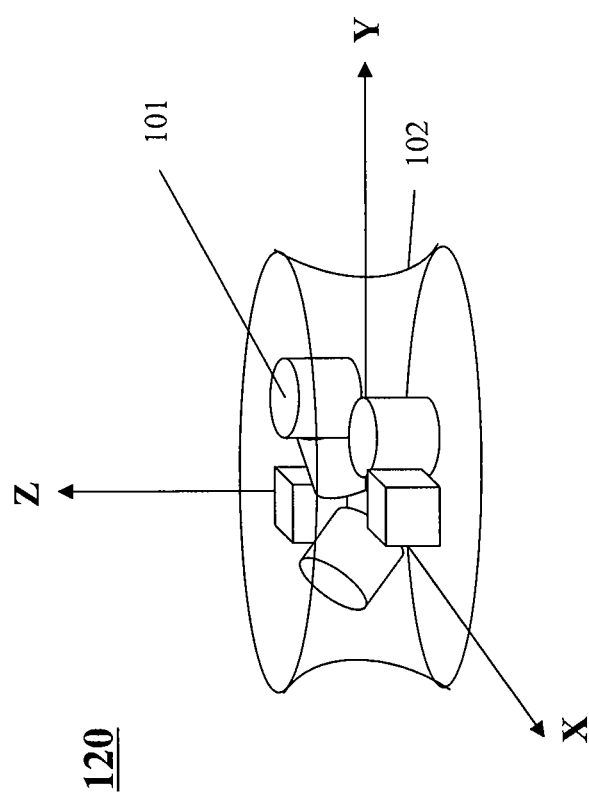
FIG. 1(b) shows a 3D volume containing 3D objects displayed in a 3D coordinate system.

The present teaching pertains to method and system for facilitating interactive placement of a needle or a probe at a target location inside a three-dimensional (3D) volume (object), possibly together with nearby supporting anatomies, rendered in a 3D space on a computer screen. The disclosed method and system may be applied in pre-surgical planning for percutaneous procedures such as radiofrequency ablation to assist medical personnel to better prepare for an accurate needle entry point or a proceeding path to enable the medical personnel to observe any potential possible complication or difficulties associated with the entry point or along the path. Three-dimensional image reconstruction allows a more intuitive 3D visualization of a patient's anatomy and makes the preoperative treatment planning more realistic and more accurate. Different facilitating means is also described for enhanced visualization of spatial relationships between organs, probes, and surrounding anatomies. FIG. 1(a) depicts a three dimensional scene with a 3D volume 100 having three dimensional objects rendered therein. As shown, the 3D volume 100 has been segmented into several objects 101-a, 101-b, ..., 101-c, and 102. These objects may correspond liver, lesions, bones, arteries, vital organs, or skin (e.g., 102). Each 3D object may correspond to a sub 3D volume within the 3D volume 100. The 3D volume 100 may be visualized on a 2D display screen such as a computer display screen. Such visualization may be performed in a well defined 3D coordinate system. This is shown in FIG. 1(b), in which the 3D volume 100 is displayed in a 3D space defined by a coordinate system 120 with three axies, X, Y, and Z. The 3D volume 100 may be rendered on a 2D display screen with respect to the 3D coordinate system 120 with a particular 3D pose, including its geometric position and orientation.

In some embodiment, the 3D volume 100 may be sliced into a plurality of 2D slices along some 3D orientation so that each of the slice provides 2D imagery of the 3D volume 100 along a certain direction. To facilitate effective 3D visualization, these 2D slices can be placed inside this 3D scene to enable a viewer to observe the composition of different objects, if any, on a planar surface. Through this means, one may be able to observe the spatial relationship among different segmented 3D objects. The concept is described in U.S. Pat. No. 7,315,304, entitled "Multiple Volume Exploration System and Method".

Figure 1C:
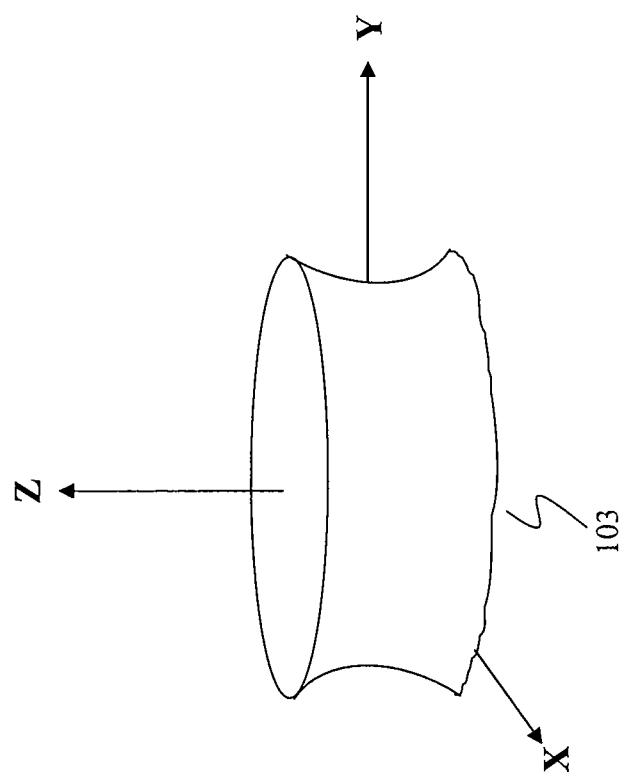
FIG. 1(c) shows a 3D volume displayed in a 3D coordinate system in an opaque mode.

A user may manipulate the visualization of the 3D volume 100 in different ways. For example, the entire 3D volume may be rotated and translated with respect to the 3D coordinate system 120. This may facilitate the user to observe the spatial relationships among different objects from different angles. In addition, the visualization of each segmented object can be independently manipulated, e.g., a 3D object may be made visible or invisible so that a user can see the areas of the 3D volume 100 where it is occluded by the selected 3D object. This may be done by adjusting the transparency of such selected 3D object. When the selected 3D object is made completely transparent or highly translucent, an object occluded by the selected 3D object can be made more visible. In some embodiments, a 3D object of interest can be made opaque and when additional 2D slices for that object are also rendered, one can be more clearly observe the internal structure of the 3D object. For example, when a 3D object corresponds to skin of a human body, when a user elects to visualize the skin in a transparent mode, all the objects inside of the skin structure can be made visible. On the other hand, if the user elects to visualizes the skin in an opaque mode, none of the 3D objects wrapped inside of the skin will not be visible. This is shown in FIG. 1(c), where the skin object 102 is visualized in an opaque mode 103 and none of the objects inside of the skin is visible. In some embodiments, the level of transparency may be adjusted gradually and interactively to meet a user's needs.

Figure 2A:
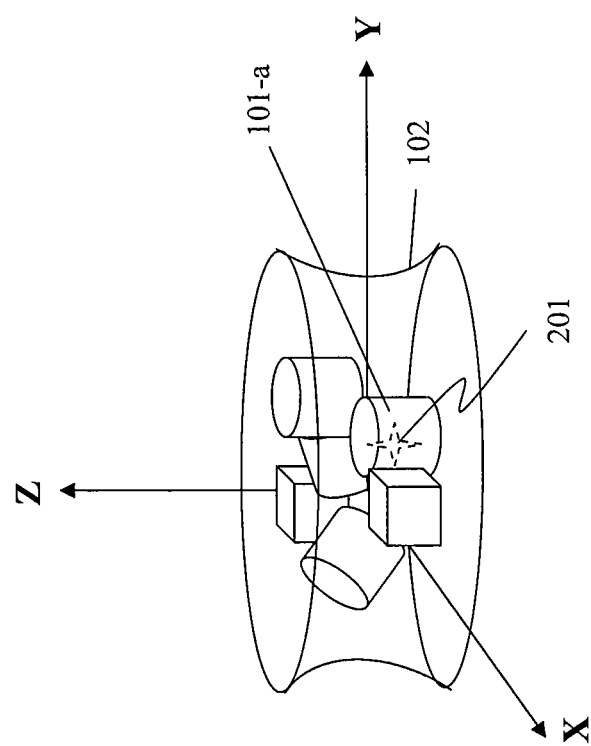
FIG. 2(a) depicts a 3D scene having 3D objects displayed therein and 3D point specified in the 3D scene for placing a virtual probe, according to an embodiment of the present teaching.

FIG. 2(a) depicts a three dimensional scene 300 having three dimensional objects displayed therein and a 3D location specified, according to an embodiment of the present teaching. To perform a percutaneous pre-operational surgical planning, a user may interactively interface with a system developed in accordance with the present teaching to specify a 3D location at which a virtual probe is to be placed. This is shown in FIG. 2(a) where a 3D location 201 is determined in accordance with a 2D position specified on a, e.g., display screen. Such a specification may be done via various known techniques such as a mouse click on a display screen. A screen point determined via, e.g., a mouse click, may correspond to a 2D coordinate with respect to a 2D coordinate system defined based on the underlying display screen. Such a 2D coordinate needs to be transformed into a 3D coordinate point in the 3D scene 300, which can be done by translating the 2D coordinate into a 3D coordinate via a transformation. Such a 2D coordinate may be selected with respect to a 3D object (e.g., skin 102) in the 3D scene and the 3D location transformed may correspond to a 3D location on the 3D object at which a virtual probe or needle is to be virtually placed in order to simulate the effect of percutaneous surgery in a percutaneous pre-operational surgical planning procedure.

Figure 2B:
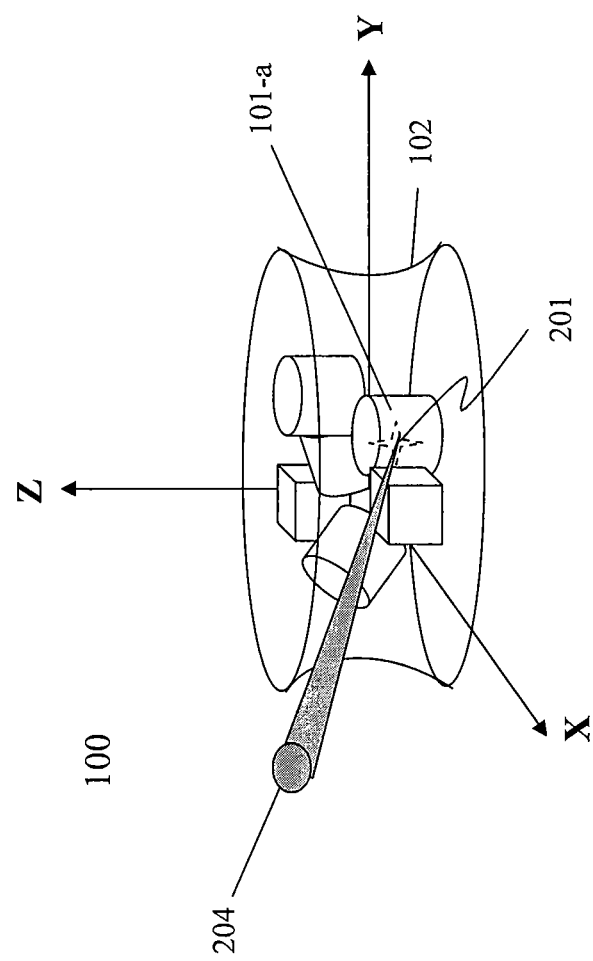
FIG. 2(b) depicts a 3D scene with a plurality of 3D objects displayed therein and a movable and adjustable probe being placed at a specified 3D point near an object, according to an embodiment of the present teaching.
Figure 3:
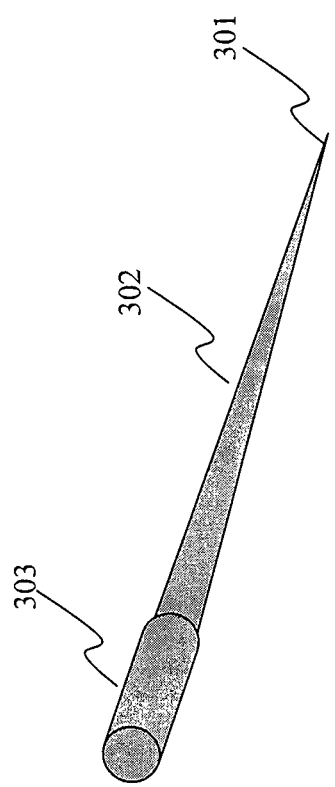
FIG. 3 shows an exemplary structure of a movable and adjustable probe, according to an embodiment of the present teaching.

FIG. 2(b) shows that once the 3D coordinate corresponding to a 2D point selected on a display screen is determined, a virtual probe or needle 204 may be virtually placed at the 3D coordinate position in the 3D space 300. The virtual probe or needle 204 may have a straight shape or any other shape as needed, as shown in FIG. 3. In some embodiments, a virtual probe may be constructed to have a tip 301, a body 302, and a handle 303. The tip 301 is where the virtual probe 204 is placed on a 3D object (e.g., object 102 in FIG. 2(b)). Through appropriate interfaces and tools (see description below with reference to FIG. 8), a user may manipulate the movement of the virtual probe 204 via certain part of the probe, e.g., the body 302 or handle 303. For example, in a precutaneous pre-operational surgical planning for liver disease, a lesion may be selected as a 3D object to which a virtual probe is to be placed (e.g., object 101-a) and the point at which the virtual probe and the human skin intersect is where a needle in real operation may need to be placed.

The virtual probe, once inserted, may be adjusted. This may be done by allowing a user to use a tool (e.g., in a GUI, use a drag and pull motion) to move different parts of the virtual probe based on needs. For example, a user may be allowed to drag the tip 301 of the probe and pull to a desired 3D location. A user may also be allowed to grab the body 302 of the probe and drag it so that the tip of the probe remains the same. Similarly, a user may be allowed to drag the handle 303 of the tip and move around. In other embodiments, a user may be allowed to move the tip by dragging the body 302 or the handle 303.

Figure 4A:
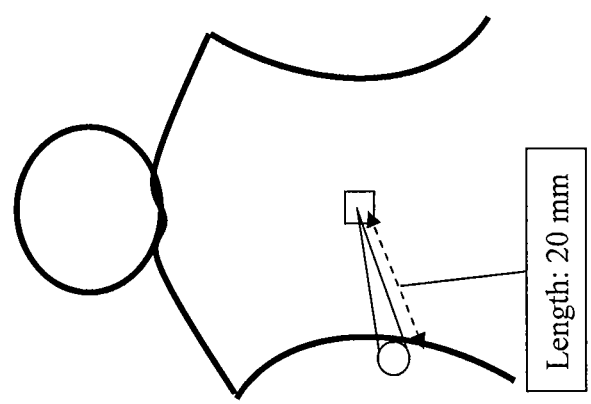
FIGS. 4(a)-4(c) show different variations associated with movable and adjustable features of a virtual probe, according to an embodiments of the present teaching.

When a virtual probe is created, it may have a certain length and such a length may be displayed along with the probe (see FIG. 4(a)). The probe length can be dynamic or fixed. A fixed-length probe may be used to mimic the commercial needle electrode systems which commonly have length of 10 cm, 15 cm, and 20 cm. Different lengths may be made available and a user may select any one of the available lengths.

Figure 4C:
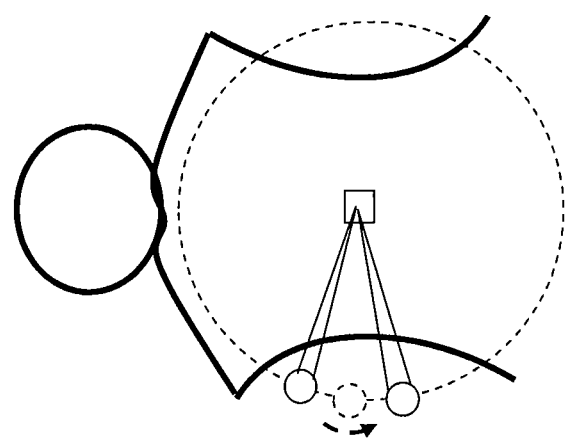

A configuration using a probe of a fixed length may be helpful in terms of having a more realistic simulation in pre-surgical planning. When a probe is configured with a fixed length, the movement of the probe may be accordingly determined. For instance, e.g., the movement of the probe may be confined to skin 102, or to a half sphere with respect to the tip of the probe when the length of the probe is fixed. This is shown in FIG. 4(c). However, when a user selects a different length for the probe, the scope of allowed movement of a probe may be accordingly or automatically adjusted.

Figure 4B:
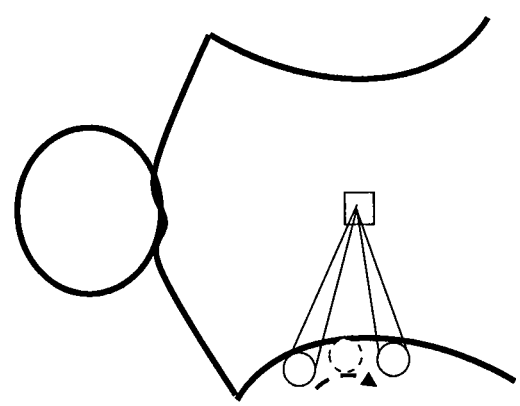

In some embodiments, the length of a probe may be made dynamic. A user can use a probe with a dynamic length as shown in FIG. 4(b). The scope of movement of a probe with a dynamic length may be defined with respect to the tip of the probe. In this case, the movement of the probe may be constrained on, e.g., a skin surface. The probe's angles with respect to a coordinate system, such as patient coordinate system, may be displayed on the screen in real-time while the probe is being manipulated.

Figure 5:
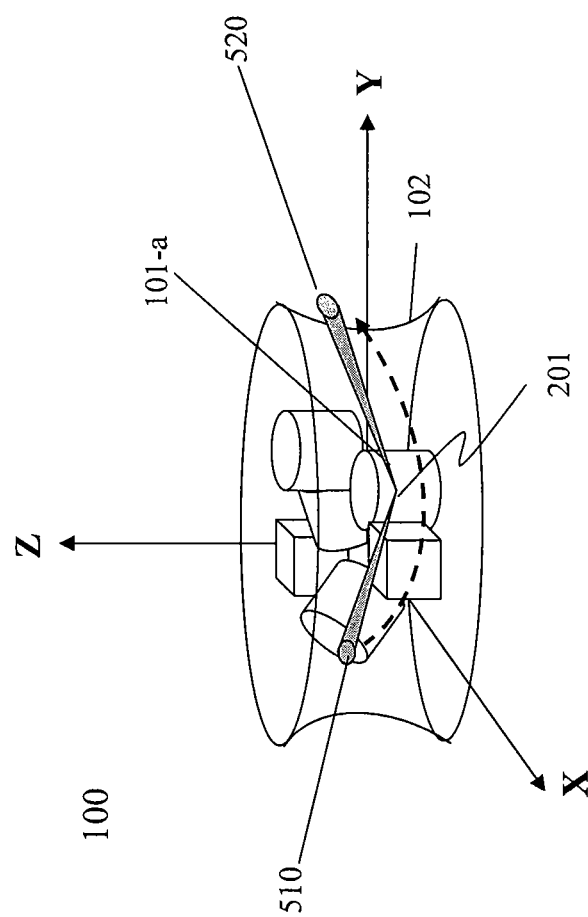
FIG. 5 illustrates multiple probes placed in a 3D volume, according to an embodiment of the present teaching.

In some embodiments, more than one probes may be placed. FIG. 5 illustrates two probes 510 and 520 being placed on the same 3D location of a selected object. This may be helpful to provide a user the ability to experiment with more than one probes simultaneously and make it possible to assess the possibility of utilizing multiple probes in the same treatment and effect thereof.

Figure 6:
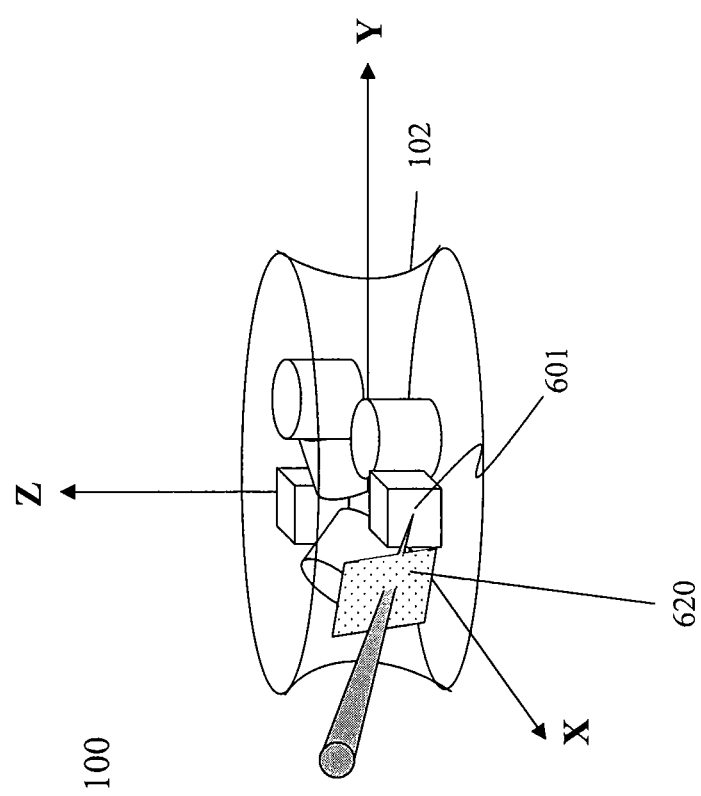
FIG. 6 depicts a probe placed near a 3D object with a 2D cross sectional view of the 3D object at a certain location of the probe to show the anatomical structure near the probe, according to an embodiment of the present teaching.
Figure 7:
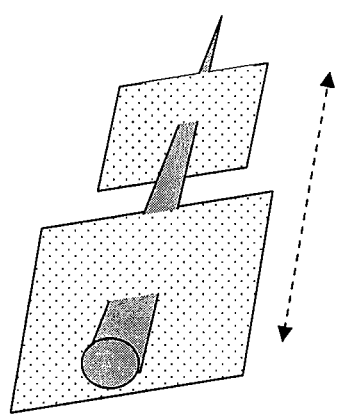
FIG. 7 illustrates the scenario in which a user can dynamically adjust the viewing of anatomical structure by sliding the cross sectional view along a probe, according to an embodiment of the present teaching.

The system according to the present teaching may also provide the means to allow a user to view the anatomical structure of a 3D object along a probe that has been placed. In FIG. 6, an orthogonal probe view 620 is provided that corresponds to a 2D slice image of the 3D object 601. This 2D slice image may be a view centered at the probe and orthogonal to the probe. Through this view, a user can see what structures are passed through by the probe in a two-dimensional image view. A user may also be allowed to move the viewing plane up and down along the probe by dragging along the probe body, as illustrated in FIG. 7. User can also activate an automatic movement function so that the probe view may automatically move up and down along the probe according to a particular time interval.

FIG. 8 illustrates the concept of detecting an obstacle encountered by a probe, according to an embodiment of the present teaching. In some medical applications, an actual or physical probe can not go through some parts of the body such as bones, vital organs, or major arteries. Such parts of the body may be categorically defined as obstacles or prohibited parts. According to the present teaching, mechanisms and method are provided to automatically detect collision when a probe intersect with such parts of the body. A system in accordance with the present teaching may define default obstacles or prohibited parts. In some embodiment, it can also provide flexible means for a user to dynamically define such obstacles according to the needs of specific applications. For instance, in some applications, bones may be an obstacle. However, in other applications, bones may be a target area for which a probe needs to be placed.

Figure 8A:
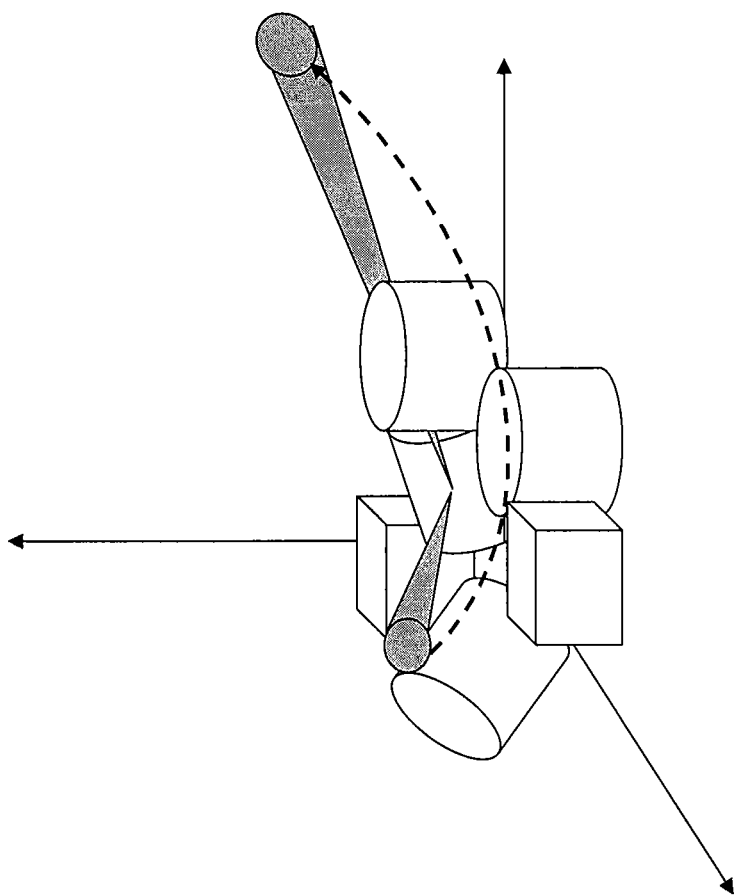
FIG. 8(a) illustrates the concept of detecting an obstacle encountered by a probe, according to an embodiment of the present teaching.
Figure 8B:
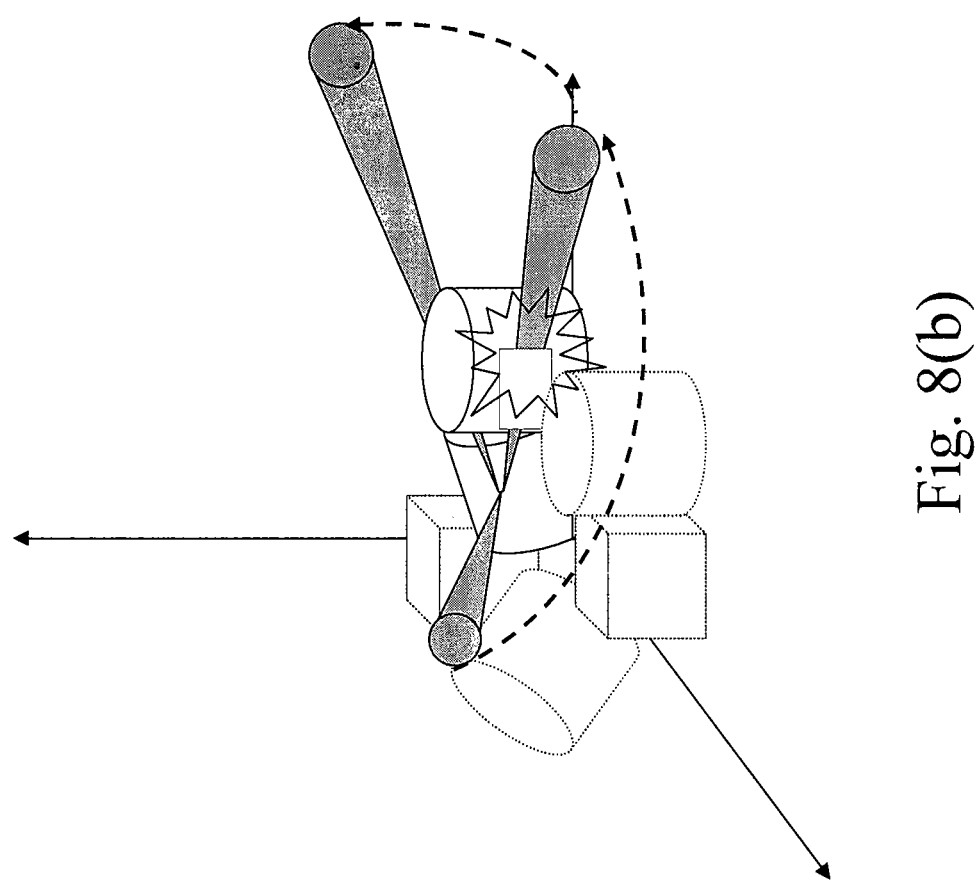
FIG. 8(b) depicts an exemplary means to generate a warning of a detected obstacle, according to an embodiment of the present teaching.

When obstacles are defined, the system may provide automatic collision detection capabilities while a probe is placed into a 3D scene. In FIG. 8(a), it is shown that whenever a probe is placed, collision detection may be applied automatically. When a user moves a probe around, whenever the probe hits any of the defined obstacles, the system may alert the user. Example ways to alert a user is to create an alarming visual effect such as using a visually stimulating color or generate an audio sound. This is illustrated in FIG. 8(b). Such a feedback is to generate a warning effect to catch the user's attention. For different obstacles, different colors or sounds may be used so that the user can recognize the type of obstacle associated with each different warning. Audio feedback may also be design to indicate orally the type of obstacle encountered.

In some embodiments, obstacles may be individually turned on or off so that a user can experiment and explore different scenarios when moving and inserting the probe.

Figure 9:
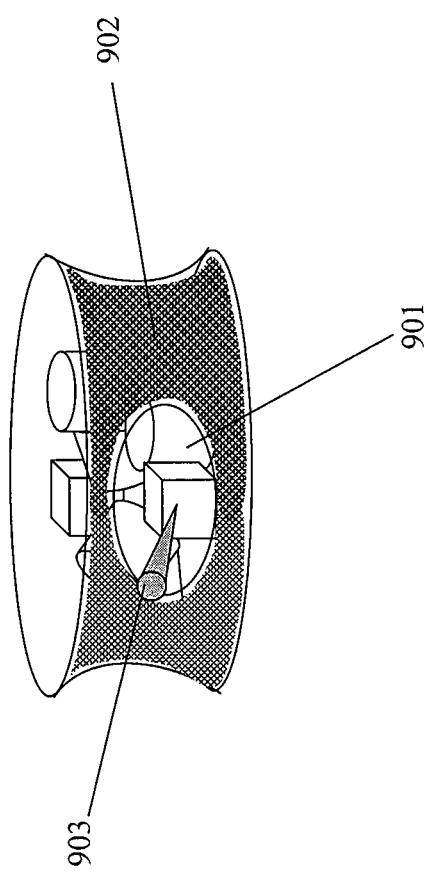
FIG. 9 presents an exemplary way to visualizing different zones for placing a probe, according to an embodiment of the present teaching.

Once obstacles or areas where a probe is prohibited to enter, it may also be possible to mark up such regions in the 3D scene as areas that the probe may not enter. For example, in some procedures, bones may be considered as obstacles. In addition, major arteries may likely be considered as areas that are constrained or prohibited regions. According to the present teaching, means may be provided to automatically identify these constrained regions and mark as such on the skin surface corresponding to such prohibited areas. This is illustrated in FIG. 9, in which the skin surface is marked as two zones. One corresponds to an area 901 where a probe 903 can enter and the other area 902 is an area where the probe 903 is not allowed. Such zones are computed with respect to a specific target position, which corresponds to a target object inside the skin where the treatment is to be delivered through an actual needle. Therefore, Zone 901 is a valid insertion zone which is the area that the probe 903 can reach a target position of the target object without encountering any obstacles or constraints. The other zone 902 is an area that the probe is obstructed by some obstacles or constraints. Different zones may be displayed using a different visual effect such as using different colors or with different appearance such as transparency.

Figure 10:
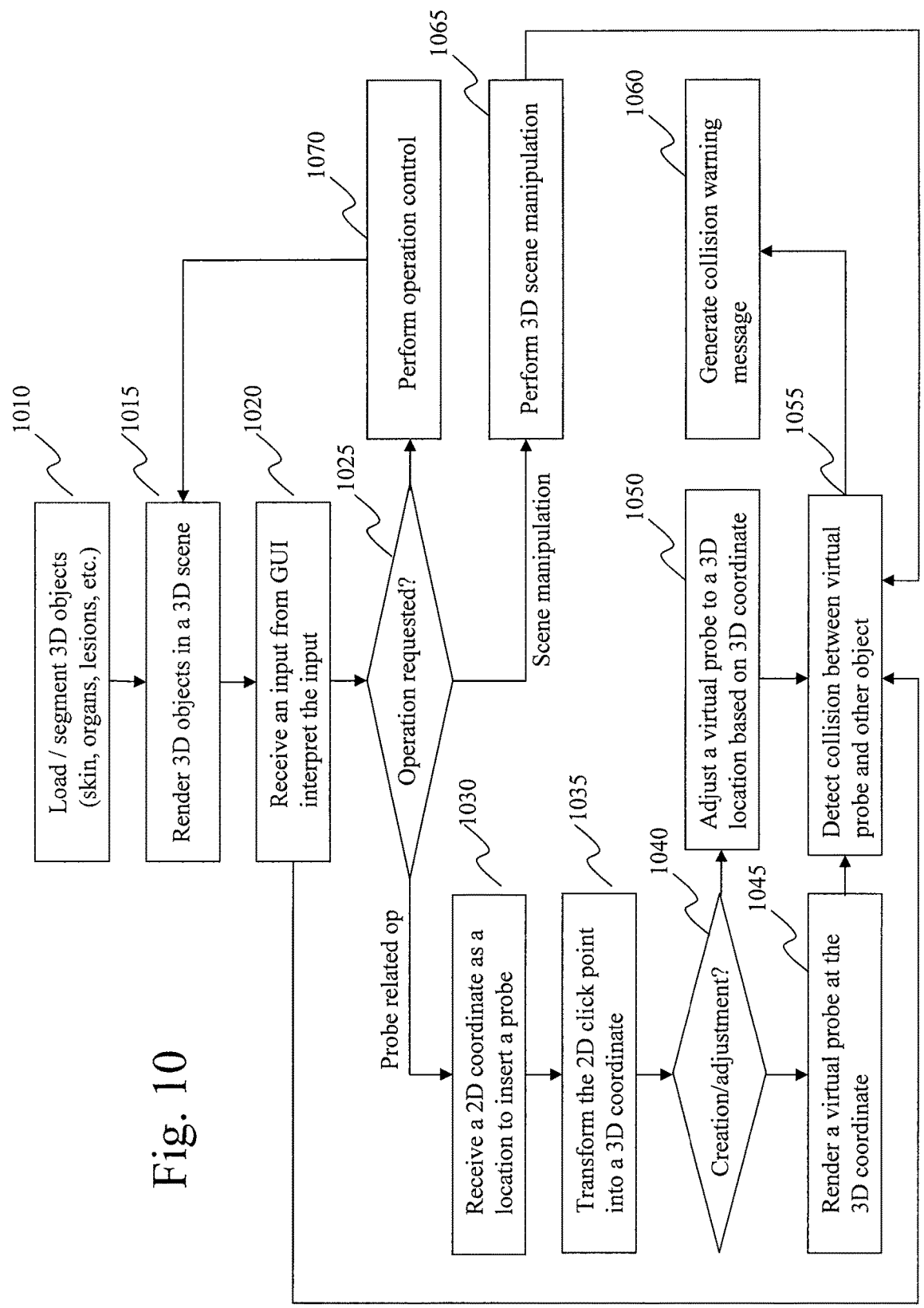
FIG. 10 is a flowchart of an exemplary process, in which a virtual probe is placed, manipulated, and rendered based on optional conditions specified by a user, according to an embodiment of the present invention.

FIG. 10 is a high level flow of an exemplary process, in which a percutaneous pre-surgical planning process is carried out, according to an embodiment of the present teaching. Volumetric data may be first loaded into a system at 1010. In some embodiments, such loaded volumetric data may be further processed, at 1010, to extract different segmented 3D objects. In some embodiment, the loaded data may have been previously segmented and one or more 3D objects may already exist. Once loaded, the 3D volume and the 3D objects contained therein are rendered in a 3D scene at 1015. After the 3D volume and the 3D objects are displayed on a display screen, a user may enter an instruction to interact with the system during a precutaneous pre-surgical planning process. A user input may be issued via different means. For instance, an input may be related to an action such as a mouse click on some control buttons or a selection of a plurality of available choices.

Such a user input may be dispatched to relative action modules according to the nature of the input or some preset system configurations. When the system receives an input, the input is interpreted at 1020. There may be different types of input. One exemplary type of input relates to definitions such as definitions of a target object, an obstacle, or a prohibited region in a 3D volume. Another exemplary type of input is an instruction related to insertion, manipulation, and visualization of different 3D objects in the process of a percutaneous pre-surgical planning.

Regarding defining different types of objects, depending on the nature of a particular procedure, a different target object may be defined. For instance, for a procedure to treat liver tumor, a lesion in a liver may identified as a target object. For each procedure, different types of obstacle may also be defined. An obstacle may be defined to be an object that a probe can not penetrate. One example of such an obstacle may be bones. However, if a different procedure requires a probe to enter into a bone structure, bones may be defined as target rather than obstacle. Another exemplary type of object is a prohibited region, which may be defined as a region that if a probe's entry may cause harm. For instance, a user may select one or more major arteries around a liver as prohibited regions to enter a probe. In this example, to allow a probe to enter into a lesion inside a liver, the probe has to take a route that avoids the bones and major arteries.

Selections of target object, obstacles, or prohibited regions may be made based on a plurality of choices, which may correspond to all the segmented 3D objects. For instance, the segmented objects in a 3D volume representing a human body may include skin, liver, pancreas, kidney, lesions inside or nearby certain organs, surrounding tissue, bones, blood vessels, etc. Depending on the procedure to be performed, a lesion associated with, e.g., the liver may be selected as a target object. Depending on the specific treatment to be performed, different obstacles or prohibited regions may be selected. For instance, for percutaneous treatment, bones may be selected as obstacles and major blood vessels may be selected as prohibited regions. Once such selections are interpreted, the system sends such definitions to a collision detection operation at 1055, which utilizes such information in automatically detecting when a probe encounters or enters into such objects.

As discussed, another type of input correspond to instructions related to insertion, manipulation, and visualization of different 3D objects. Different types of instructions may be further recognized. If the input instruction relates to insertion of a virtual probe, determined at 1025, the system further receives, at 1030, a 2D coordinate corresponding to a screen location specified by a user as where a probe is to reach. To translate the 2D screen location to a 3D coordinate at which a probe is to reach, a transformation between the 2D coordinate and a 3D coordinate is performed at 1035. Since a received 2D coordinate may correspond to either a user's desire to insert a new probe or to make an adjustment to an already inserted probe, it is further determined, at 1040, whether the operation requested corresponds to creation of new probe or adjusting an existing probe.

If the user's request is to insert a new probe, the system renders, at 1045, a new probe at the transformed 3D coordinate. The process then proceeds to detecting, at 1055, a potential collision between the probe and any other object that has been defined as either an obstacle or a prohibited region. If the user's request is to make an adjustment to an existing probe, the system adjusts, at 1050, the existing probe to the transformed 3D coordinate and then proceed to collision detection at 1055. When a collision is detected, the system may generate a warning message, at 1060, to caution the user that the probe may have encountered some obstacle or entered into a prohibited region. The manner the warning message is generated and presented may depend on the system setting. For example, the system may be defaulted to flash on the location where the collision is detected (see FIG. 8(*b*)).

When there are multiple existing probes, an additional step (not shown) may be performed, in which the user and the system may interactively determine which probe is to be adjusted. In addition, the 2D coordinate received from the user may correspond to a manipulation with respect to the tip, the body, or the handle of a probe, depending on, e.g., what is the closest part and which mode of operation the system is placed under (not shown). For example, if the system is set in a mode in which a probe is to be manipulated using the handle of the probe, then the 3D coordinate transformed from the 2D coordinate received from the user is where the handle of the probe is to be re-located. If the probe is selected to have a fixed length, then the 3D coordinate needs also to be determined based on the fact that the handle of the probe has to be on a sphere centered around the tip of the probe. A user can also switch between different modes of operation. For instance, a user may elect first to adjust the probe's tip to a best location by manipulating with respect to the tip of the probe. Once the tip location satisfies the needs of a procedure, the user may then switch to a mode in which the manipulation of the probe is through the handle of the probe. Through such manipulation via the handle of the probe, the user may adjust the entry point of the probe on the skin, without affecting the tip position, to avoid any obstacle or prohibited regions.

If the input instruction relates to 3D scene manipulation, determined at 1025, the system proceeds to 1065 to handle 3D scene manipulation. 3D scene manipulation may include object oriented scene rotation, zooming, visualization mode, etc. In some embodiments, when a 3D scene is moved around, a probe that has been inserted into the 3D scene may be moved around accordingly. In this way, a user may be able to observe the spatial relationship between the probe and surrounding objects from different angles. In some embodiments, through 3D manipulation, a user may manipulate the visibility of individual object by, e.g., making them transparent, opaque, or translucent. In some situation, a user may also control to view a 2D cross sectional view of an object along the probe and may arbitrarily change the location at which a 2D cross sectional view is generated and displayed. In other embodiment, a user may also be able to manipulate the 3D scene via the probe by, e.g., dragging the handle of the probe to rotate the entire 3D scene.

In some embodiments, it can also set that manipulation to a 3D scene does not affect the 3D pose of the probe. This may be useful at times because the user can adjust the 3D volume, e.g., so that or until a collision is avoided. In this case, whenever the 3D scene is changed (e.g., rotated or translated), the system automatically proceeds to 1055 to detect collisions and subsequently report a collision at 1060 if it is detected.

Figure 11:
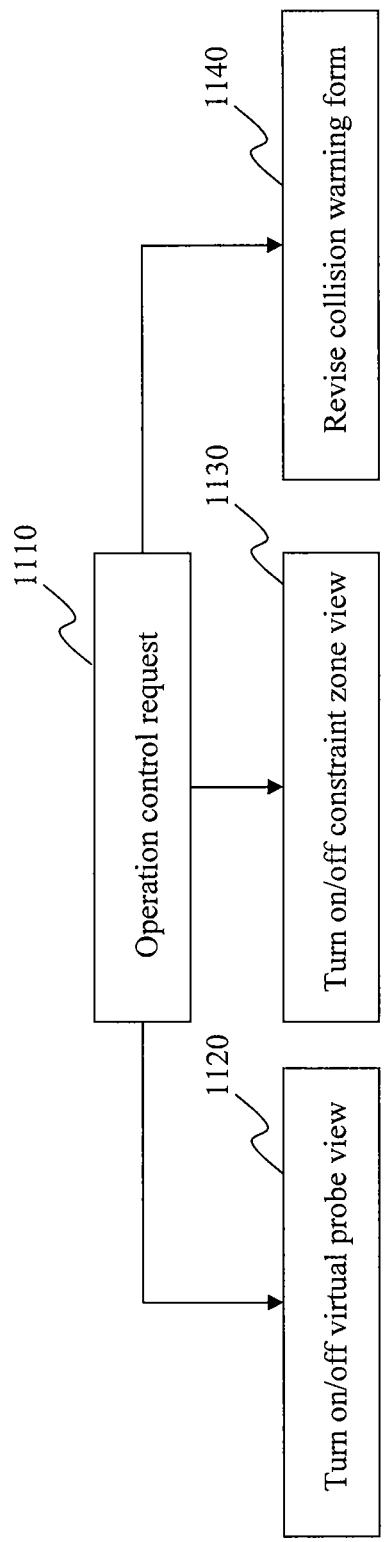
FIG. 11 illustrates exemplary types of operational control in percutaneous pre-surgical planning, according to an embodiment of the present teaching.

If the input instruction relates to operational control, determined at 1025, the system proceeds to 1070 to perform instructed control. There may be different types of operational controls. FIG. 11 illustrates some exemplary types. For instance, a user may control to turn on or off of the view of the virtual probe (1120). A user may also control to turn on or off the view in which different zones associated with certain constraint may be visually distinct (1130). A user may also control how a collision situation may be presented, e.g., visually or acoustically (1140). In addition, as discussed earlier, a user may also control how to display a 3D object, e.g., opaque or transparent. This includes to control the display of each individual object or the entire 3D scene.

Figure 12:
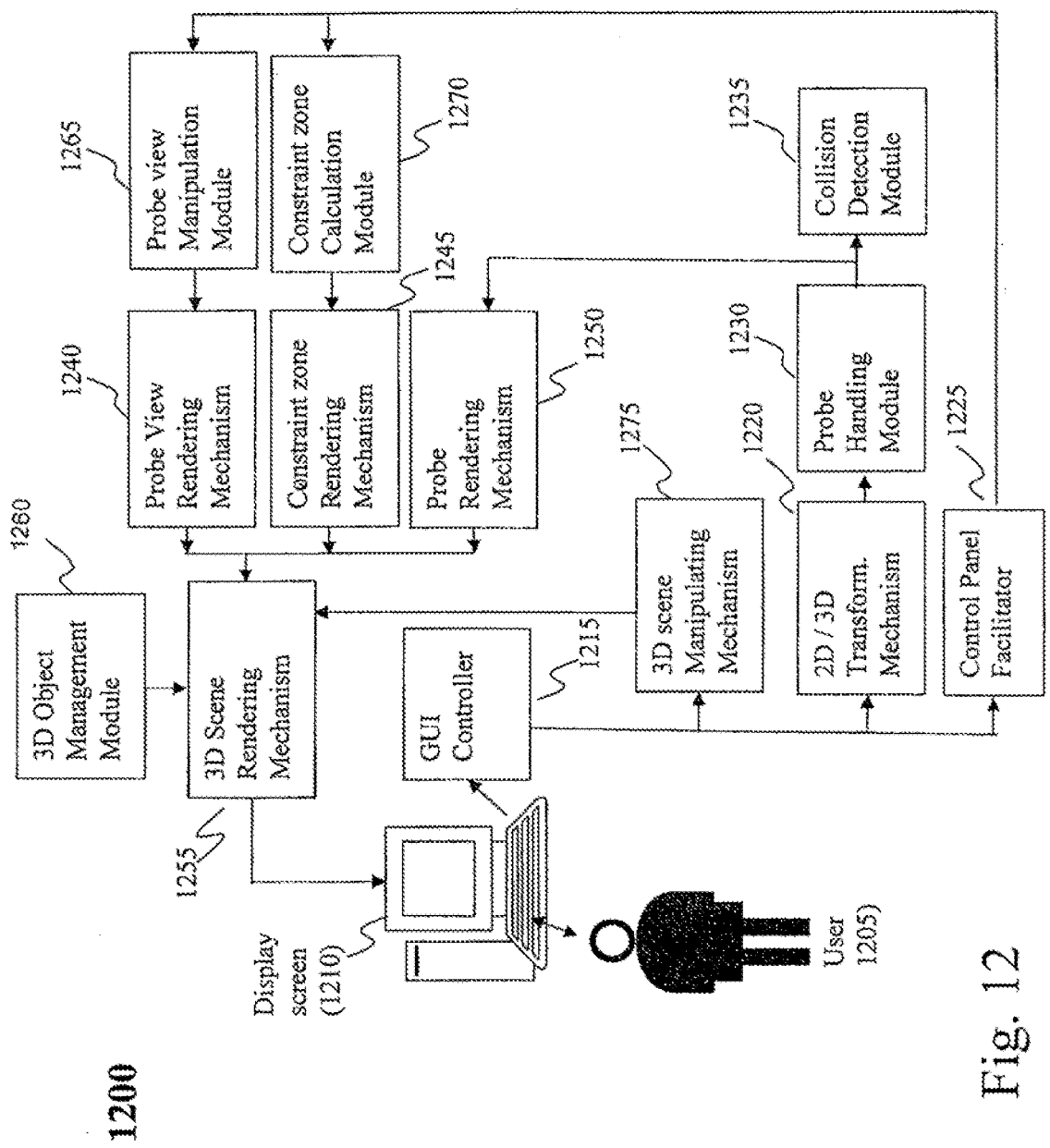
FIG. 12 depicts an exemplary construct of a system that facilitates 3D placement and manipulation of a virtual probe in a 3D environment, according to an embodiment of the current invention.

FIG. 12 depicts a construct of an exemplary system 1200 that facilitates the placement and manipulation of a virtual probe in a 3D environment for percutaneous pre-operational surgical planning, according to an embodiment of the current invention. The system 1200 comprises a display device 1210, a graphical user interface 1215, a 2D/3D transformation mechanism 1220, a control panel facilitator 1225, a probe handling module 1230, a collision detection module 1235, a plurality of rendering mechanisms, including a probe view rendering mechanism 1240, a constraint zone rendering mechanism 1245, a probe rendering mechanism 1250, and a 3D scene rendering mechanism 1255, a 3D object management module 1260, a probe view manipulation module 1265, a constraint zone calculation module 1270, and a 3D scene manipulating mechanism 1275.

A user 1205 may interact with the system 1200 via a user interface displayed on the display device 1210. The GUI controller 1215 may control interaction between the system 1200 and user 1205. If the user 1205 desires to use a tool associated with a virtual probe once a 3D scene is set up, the user may request the system to retrieve 3D object information from the 3D object management 1260 and render such objects via the 3D scene rendering mechanism 1255. When such user request is entered via the user interface, the GUI controller 1215 may then interpret the request and accordingly activates appropriate functional modules to perform the requested operations.

For example, if request is to change the orientation of the 3D scene, the system may activate the 3D scene manipulator module 1275 to modify the orientation of the 3D scene based on the specification from the user. During this process, the user and the GUI controller may continuously interact, e.g., user may click a point in the 3D scene and drag along a certain direction so that the entire 3D scene may move along in the same direction. Similarly, the user may exercise the same control with respect to a particular 3D object such as a virtual probe.

A user may also interact with the system to exercise various controls over a probe. When the user manually controls a probe via a 2D display screen, the 2D/3D transformation mechanism 1220 dynamically transforms a 2D screen point to a 3D point in the 3D scene, and then pass the 3D point to the probe handling module 1230 which determines whether it is a new probe creation operation or an adjustment operation to be made to an existing probe. The desired probe is then rendered in the 3D scene by the probe rendering mechanism 1250. In the process of moving an existing probe, the collision detection module 1235 is operative to detect intersection between the applicable probe and any 3D objects that have been defined as either an obstacle or prohibited regions. The collision detection module 1235 may also generate warning information when a collision is detected.

As discussed herein, the system also provides the means for a user to exercise various control regarding the operation of the system. For example, via the control panel facilitator 1225, a user may activate or deactivate a probe view controlled by the probe view manipulation module 1265. A user may also control other visualization parameters such as transparency through the probe view rendering mechanism 1240. A user may also set desired mode of display which may also be personalized and such a setting may be applied automatically when the user signs up with the system. For example, a user may desire to always have the skin (a 3D object) displayed in a transparent mode. Another user may desire to have a particular sound as a warning whenever a collision is detected. A user may also control the activation or deactivation of computation of a constraint zone by interacting with the constraint zone calculation module 1270 or control the display of a detected constraint zone by interacting with the constraint zone rendering mechanism 1245.

While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A method implemented on a computer system having at least a processor, storage, and display for interactive percutaneous pre-operational surgical planning, the method comprising:
    rendering, by the processor, a three dimensional (3D) volume and one or more 3D objects in the 3D volume on a two dimensional (2D) computer display screen, wherein the one or more 3D objects are one of a surgical target type and an obstacle type;
    receiving, by the processor, information associated with a 3D location specified with respect to one of the one or more 3D objects in the surgical target type;
    rendering, by the processor, a 3D virtual probe at the 3D location;
    receiving, directly through a physical computer input device operating in a 2D space, information associated with an operation in the 2D space performed by a user via the physical computer input device;
    dynamically adjusting, by the processor, a 3D pose of the 3D virtual probe in the 3D volume, wherein the 3D pose is dynamically transformed from a 2D location on the 2D computer display screen and the information associated with the operation in the 2D space;
    rendering, by the processor, a 2D image of the surgical target type 3D object, the 2D image being centered at the tip of the 3D virtual probe and displayed orthogonally, along a length of the 3D virtual probe;
    dynamically detecting, by the processor, a collision between the 3D virtual probe and one of the one or more 3D objects of the obstacle type during the dynamic adjustment of the 3D pose of the 3D virtual probe; and
    providing a notification of the detected collision to the user, wherein dynamically adjusting the 3D pose of the 3D virtual probe comprises
        rotating the 3D virtual probe based on a movement of a part of the 3D virtual probe, wherein the part of the 3D virtual probe is adapted to move in an unrestricted manner along any direction on a surface of a half sphere of the 3D volume, wherein a size of the half sphere is determined based on the 3D location and a length of the 3D virtual probe.

2. The method according to claim 1, wherein the part of the 3D virtual probe includes at least one of a probe end, a probe body, and a probe handle.

3. The method according to claim 2, wherein the 3D pose of the 3D virtual probe can be adjusted via at least one of the handle and the body of the 3D virtual probe.

4. The method according to claim 1, wherein the 3D virtual probe is placed so that the tip of the virtual probe is placed at the 3D location.

5. The method according to claim 1, wherein the 3D pose of the 3D virtual probe includes a coordinate of the tip of the 3D virtual probe and the 3D orientation of the 3D virtual probe.

6. The method according to claim 1, wherein
    the one or more 3D objects include a tumor, an organ, bone, and tissue; and
    the boundary of the 3D volume corresponds to skin.

7. The method according to claim 1, wherein the surgical target type includes a tumor of a pre-defined type.

8. The method according to claim 1, further comprising generating information that describes a spatial relationship between the 3D virtual probe and the 3D object in the surgical target type.

9. The method according to claim 8, wherein the spatial relationship includes within, outside, or touch.

10. The method according to claim 1, wherein the 3D volume is rendered in an opaque mode so that the one or more 3D objects in the 3D volume are not visible.

11. The method according to claim 1, wherein the 3D volume is rendered in a transparent mode so that the one or more 3D objects in the 3D volume can be made visible.

12. The method according to claim 1, further comprising generating information associated with an estimated effect on the 3D object in the surgical target type caused by insertion of the 3D virtual probe into the 3D object in the surgical target type.

13. The method according to claim 1, wherein the 3D virtual probe can be further adjusted in terms of its length.

14. The method according to claim 1, wherein
    dynamically adjusting the 3D pose of the 3D virtual probe further comprises moving at least a part of the 3D virtual probe in the 3D volume by allowing the user to, directly through the operation in the 2D space performed via the physical computer input device, grab the part of the 3D virtual probe and drag the part of the 3D virtual probe along a direction.

15. The method of claim 1, further comprising:
rendering another 3D virtual probe at the 3D location; and
dynamically adjusting a 3D pose of the other 3D virtual probe in the 3D volume directly through the physical computer input device operating in the 2D space, wherein
dynamically adjusting the 3D pose of the other 3D virtual probe comprises:
   moving at least a part of the other 3D virtual probe in the 3D volume by allowing the user to, directly through the operation in the 2D space performed via the physical computer input device, grab the part of the other 3D virtual probe and drag the part of the other 3D virtual probe along a direction, and
   rotating the other 3D virtual probe by allowing the user to, directly through the operation in the 2D space performed via the physical computer input device, grab a part of the other 3D virtual probe and rotate the part of the other 3D virtual probe with a movement confined onto a surface of a half sphere of the 3D volume with respect to a tip of the 3D virtual probe such that a 3D orientation of the 3D virtual probe is changed and a relative position between the other 3D virtual probe and the one or more 3D objects is changed.

16. The method of claim 1, wherein the notification of the detected collision is provided by one of a visual effect and an audible signal, the notification being determined based on the 3D object.

17. The method of claim 1, wherein the 2D image is slidable along the length of the virtual probe.

18. A system for interactive percutaneous pre-operational surgical planning, comprising:
   a 3D rendering mechanism implemented on a processor of a computer and configured for rendering a 3D volume and one or more 3D objects in the 3D volume on a 2D computer display screen, wherein the one or more 3D objects are one of a surgical target type and an obstacle type;
   a user interface controller implemented on the processor and configured for receiving, directly through a physical computer input device operating in a 2D space, first information from a user specifying a 3D location with respect to one of the one or more 3D objects in the surgical target type and second information associated with an operation in the 2D space performed by the user via the physical computer input device;
   a probe manipulation mechanism implemented on the processor and configured for
      rendering a 2D image of the surgical target type 3D object, the 2D image being centered at the tip of the 3D virtual probe and displayed orthogonally, along a length of the 3D virtual probe, and
      rendering the 3D virtual probe at the 3D location and dynamically adjusting a 3D pose of the 3D virtual probe in the 3D volume, wherein the 3D pose is dynamically transformed from a 2D location on the 2D computer display screen and the second information associated with the operation in the 2D space;
   a collision detection mechanism implemented on the processor and configured for dynamically detecting a collision between the 3D virtual probe and one of the one or more 3D objects of the obstacle type during the dynamic adjustment of the 3D pose of the 3D virtual probe; and
   an information generation mechanism implemented on the processor and configured for providing a notification of the detected collision to the user, wherein
   the probe manipulation mechanism is further configured for
      rotating the 3D virtual probe based on a movement of a part of the 3D virtual probe, wherein the part of the 3D virtual probe is adapted to move in an unrestricted manner along any direction on a surface of a half sphere of the 3D volume, wherein a size of the half sphere is determined based on the 3D location and a length of the 3D virtual probe.

19. The system according to claim 18, wherein the information generation mechanism comprises a constraint calculation module configured for identifying one or more zones in the 3D volume in accordance with the 3D pose of the virtual 3D probe.

20. The system according to claim 19, wherein the one or more zones include a zone that represents an obstacle for the virtual 3D probe to enter.

21. The system according to claim 20, wherein the obstacle includes an object corresponding to a bone.

22. The system according to claim 19, wherein the one or more zones include a zone that represents a prohibited region where the virtual 3D probe is not permitted to enter.

23. The system according to claim 22, wherein the prohibited region includes a 3D object corresponding to an artery.

24. The system according to claim 18, wherein
dynamically adjusting the 3D pose of the 3D virtual probe further comprises moving at least a part of the 3D virtual probe in the 3D volume by allowing the user to, directly through the operation in the 2D space performed via the physical computer input device, grab the part of the 3D virtual probe and drag the part of the 3D virtual probe along a direction.

* * * * *